(12) United States Patent
Tomkoria

(10) Patent No.: US 10,327,719 B2
(45) Date of Patent: *Jun. 25, 2019

(54) SENSOR HOLDING APPARATUS FOR FACILITATING DENTAL IMAGING

(71) Applicant: Anita Tomkoria, Newport Coast, CA (US)

(72) Inventor: Anita Tomkoria, Newport Coast, CA (US)

(*) Notice: Subject to any disclaimer, the term of this patent is extended or adjusted under 35 U.S.C. 154(b) by 407 days.

This patent is subject to a terminal disclaimer.

(21) Appl. No.: 14/980,611

(22) Filed: Dec. 28, 2015

(65) Prior Publication Data
US 2016/0128655 A1 May 12, 2016

Related U.S. Application Data

(63) Continuation-in-part of application No. 14/151,734, filed on Jan. 9, 2014, now Pat. No. 9,247,916.

(51) Int. Cl.
*A61B 6/14* (2006.01)
*A61B 6/00* (2006.01)

(52) U.S. Cl.
CPC ............ *A61B 6/145* (2013.01); *A61B 6/4233* (2013.01)

(58) Field of Classification Search
CPC ......... A61B 6/145; A61B 6/4233; A61B 6/14; A61B 6/4423; A61B 6/4435; A61B 6/587; A61B 6/4283; A61B 6/08; A61B 6/425; A61B 2560/0233; A61B 6/4429; A61B 6/461; A61B 6/508; A61B 6/06; A61B 6/44; A61B 6/03; A61B 2560/0456; A61B 5/121; A61B 6/42; A61B 1/05; A61B 1/24; A61B 6/462; A61B 6/548; A61B 6/563; A61B 10/0096; A61B 10/0275; A61B 10/04; A61B 1/00165; A61B 1/015; A61B 2010/045; A61B 2560/0475;
(Continued)

(56) References Cited

U.S. PATENT DOCUMENTS 4,507,798 A * 3/1985 Welander ............. G03B 42/042
378/168
5,044,009 A 8/1991 Klauser
(Continued)

FOREIGN PATENT DOCUMENTS

WO WO2003065895 8/2003

*Primary Examiner* — Irakli Kiknadze
(74) *Attorney, Agent, or Firm* — Jafari Law Group, Inc.

(57) ABSTRACT

A sensor holding apparatus for facilitating dental imaging, in accordance with one embodiment of the present invention, comprises a handle, an elongated shaft, and a sensor holder. The holder includes a coupling component configured to removably attach to a portal end of the shaft. The shaft comprises a cross-section adapted to receive a user's bite, the cross-section having a substantially polygonal perimeter to aid manipulation of the sensor inside the patient's mouth. The sensor holder further comprises a substantially flat body having a substantially flat surface adapted for removably attaching a sensor to the sensor holder. Furthermore, the substantially flat surface of the body of the sensor holder may comprise at least one edge that is adapted for removably attaching the sensor to the sensor holder by a pressure, or the sensor holder may be configured to receive an adhesive for removably attaching the sensor to the sensor holder.

20 Claims, 10 Drawing Sheets

(58) Field of Classification Search
CPC .......... A61B 2560/0487; A61B 5/0071; A61B
5/0073; A61B 6/04; C10M 135/30; C10M
135/36; C10M 129/10; C10M 133/12;
C10M 137/00; C10M 135/00; C10M
141/00; C10M 163/00; C10M 159/22;
C10M 159/24; C10M 2203/06; C10M
2205/00; C10M 2205/022; C10M
2205/026; C10M 2205/14; C10M
2207/023; G03B 42/042
USPC .................................. 378/167, 168, 191, 38
See application file for complete search history.

(56) References Cited

U.S. PATENT DOCUMENTS

| | | | |
|---|---|---|---|
| 5,652,779 A | 7/1997 | Levy | |
| 6,343,875 B1 | 2/2002 | Eppinger | |
| 6,461,038 B2 | 10/2002 | Pellegrini | |
| 6,520,676 B1 | 2/2003 | Scmitz | |
| 6,811,312 B2 | 11/2004 | Bratslaysky | |
| 6,905,244 B2 | 6/2005 | Kilcher | |
| 6,974,253 B2 | 12/2005 | Ihalainen | |
| 7,004,627 B2 | 2/2006 | Strong | |
| 7,033,075 B2 | 4/2006 | Landis | |
| 7,070,326 B2 | 7/2006 | Manley | |
| 7,097,356 B2 | 8/2006 | Calderwood | |
| 7,195,395 B2 | 3/2007 | Quarry | |
| 7,226,208 B2 | 6/2007 | Schmulenson | |
| 7,261,463 B2 * | 8/2007 | Becht | A61B 6/145 378/168 |
| 7,290,928 B2 | 11/2007 | Calderwood | |
| 7,425,095 B2 | 9/2008 | Schmulenson | |
| 7,517,148 B2 | 4/2009 | Ceisel | |
| 7,607,830 B2 | 10/2009 | Schmulenson | |
| 7,607,831 B2 | 10/2009 | Schmulenson | |
| 7,661,880 B2 | 2/2010 | Calderwood | |
| 7,695,191 B1 | 4/2010 | Buchanan | |
| 7,819,579 B2 | 10/2010 | Schmulenson | |
| 7,844,092 B2 | 11/2010 | Crucs | |
| 7,866,883 B2 * | 1/2011 | Machado | A61B 6/14 378/168 |
| 7,959,354 B2 | 6/2011 | Schmulenson | |
| 7,959,355 B2 | 6/2011 | Stantchev | |
| 8,016,483 B2 | 9/2011 | Steward | |
| 8,177,428 B2 | 5/2012 | Steck | |
| 8,333,507 B2 | 12/2012 | Schmulenson | |
| 8,500,328 B2 | 8/2013 | Frampton | |
| 2002/0176539 A1 * | 11/2002 | Da Rold | G03B 42/042 378/168 |
| 2005/0190889 A1 * | 9/2005 | Sisto | A61B 6/145 378/168 |
| 2005/0226390 A1 * | 10/2005 | Ihalainen | A61B 6/14 378/191 |
| 2010/0166151 A1 | 7/2010 | Schmulenson | |
| 2013/0244816 A1 * | 9/2013 | Lignelli | A63B 60/10 473/513 |

* cited by examiner

FIG. 1(a)
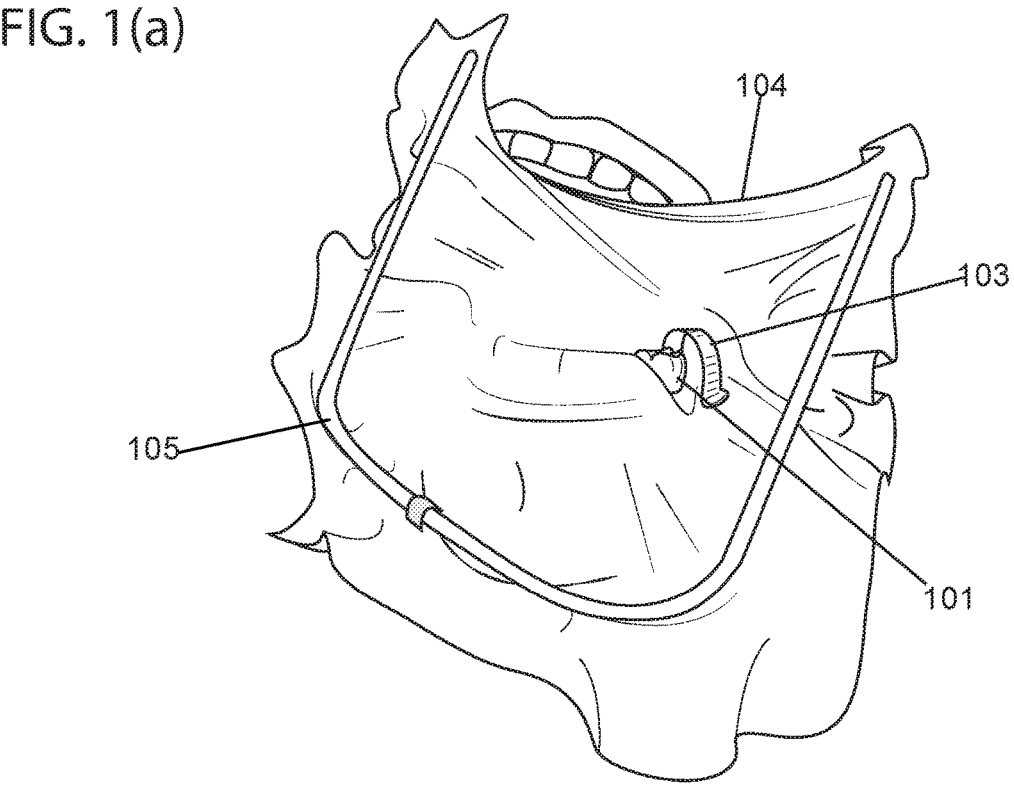
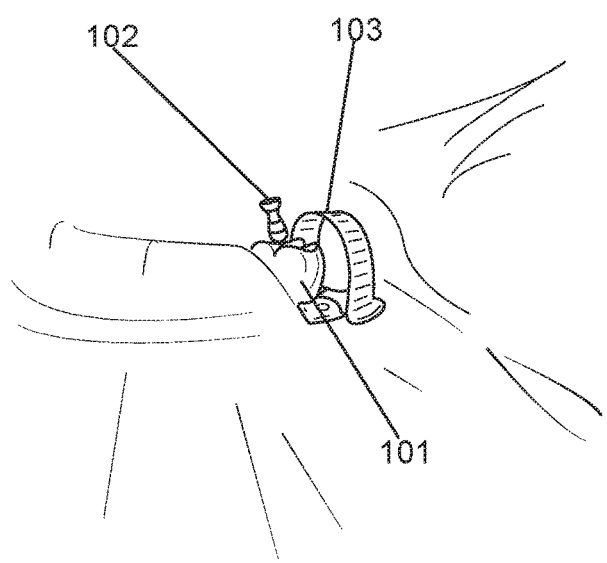
FIG. 1(b)

FIG. 3(a)
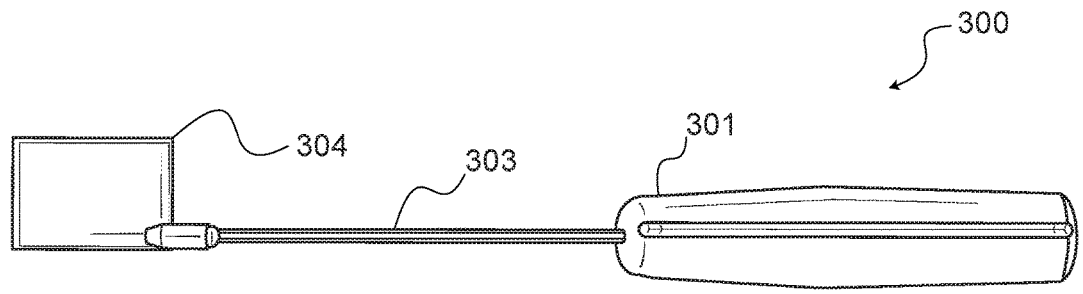
FIG. 3(b)
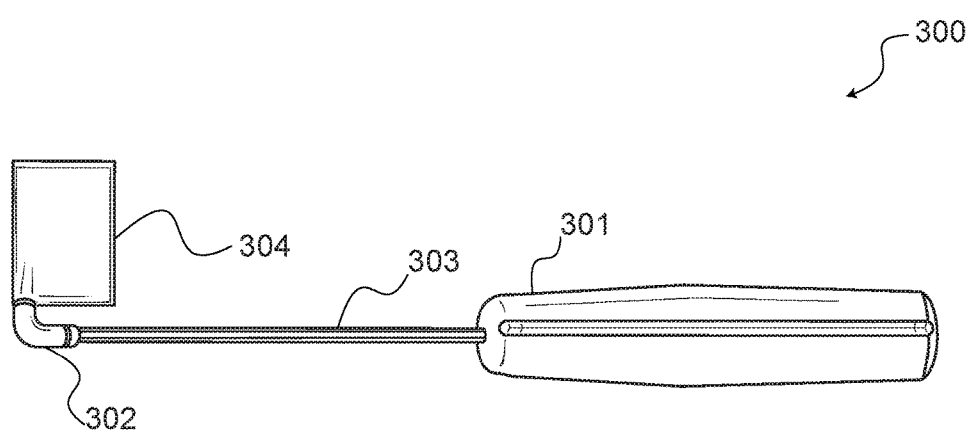
FIG. 3(c)
FIG. 3(d)
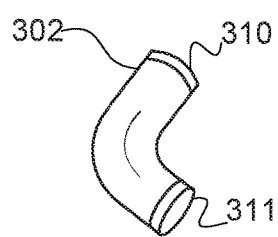
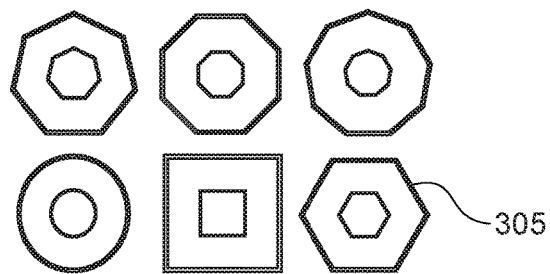

SENSOR HOLDING APPARATUS FOR FACILITATING DENTAL IMAGING

PRIORITY NOTICE

This present application is a continuation-in-part of, and claims the benefit under 35 U.S.C. § 120 to, U.S. Non-provisional patent application Ser. No. 14/151,734, filed on Jan. 9, 2014, the disclosure of which is incorporated herein by reference in its entirety.

TECHNICAL FIELD OF THE INVENTION

The present invention relates generally to a sensor holding apparatus for dental imaging and more specifically to an apparatus for holding a sensor, which may be placed inside a patient's oral cavity for use in dental imaging. The apparatus comprises a removable sensor holder that implements a specialized shaft to circumvent the need for commonly used biteplates, thereby increasing the working space available to the dental practitioner performing a procedure in the oral cavity.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Dental radiographs are x-rays used by medical professionals to ascertain detailed images of a patient's mouth so as to better identify dental disease. These radiographs are taken utilizing x-ray units, which include an x-ray tube or cone adjacent to an x-ray sensing device, and which is parallel to the area of interest in the oral cavity. The x-ray is directed perpendicular to the area and to the sensing device. X-ray sensing devices typically include x-ray film, digital sensors, phosphor plates and other related technologies that would be known by a person of ordinary skill in the art. These sensing devices are in a flat and commonly rectangular or elongated configuration, and can be placed into the oral cavity.

The x-ray sensing devices may be placed in the oral cavity in different ways to view various perspectives, orientations, and locations. For instance, a periapical placement displays the anterior or posterior tooth or teeth; included in the image is the tip of the root. Alternatively, a bitewing placement displays the central area around which the top and bottom set of teeth make contact with one another, additionally showing the crown of the imaged tooth. These placements can then be subdivided into right and left as well as maxillary and mandibular. Additionally, sensors may be placed such that images are taken in a vertical or horizontal direction depending on the desired depth or width of the desired field of view.

Recently, advancements in dentistry have shifted the focus from using x-ray film to digital sensors due in part to a decrease in the amount of x-rays (i.e. radiation) these sensors require the patient to be exposed to, as well as their convenient compatibility with electronic devices such as computers. The emergence of digital sensor devices has prompted creation of a respective field known as digital dental radiography.

Traditional holding mechanisms for x-ray film could be designed to clamp or pinch the thin x-ray film to keep it in place. However, this method cannot be utilized in digital sensors, which are thicker due to their imbedded technology. Moreover, digital sensors are more fragile and expensive and therefore must be handled very carefully. Makers of sensor holders adjusted for this change in a number of different ways. Many methods utilize a large biteplate as well as a ring and rod mechanism, wherein the rod is inserted perpendicular to the sensor holder and a ring slides through the holder, whereby the x-ray cone is properly aligned. Let biteplate be construed as part of a phosphor plate, film or digital x-ray sensor holder or sensor wherein a patient bites down on it in order to properly orient the plate, film, or sensor. While this design may be utilized when taking x-rays for routine examination, it is cumbersome to use during root canal procedures or other procedures involving obstructions within or surrounding the oral cavity.

In such cases, a device that employs a typical biteplate is not useful in such circumstances because the patient is not able to bite down on the biteplate due to the extreme pain in the tooth or due to the obstructions necessitated by many procedures, some of which include dental clamps, rubber dams, or files. This problem is further compounded by the ongoing concern that the operating field may become contaminated.

A rubber dam comprises a flexible sheet of latex or silicone and is a mandatory component of many procedures including root canals. The rubber dam creates a sterile environment within the tooth being treated by preventing bacteria and other contaminants from entering the patient's tooth from within the oral cavity. It also protects the oral cavity and the patient's airway by preventing medicaments as well as other materials used during the procedure from entering. A rubber dam is secured in a proper position around the tooth by placing it over a clamp and around the tooth. During root canal procedures, it is necessary to manipulate the rubber dam to take multiple radiographs to acquire appropriate measurements of the width and depth of the infected or aggravated areas which need cleaning and reshaping. To accomplish this, the sensor or film device has to be placed between the oral cavity and the underside of the rubber dam adjacent to the tooth being treated. When traditional sensor holders are utilized to achieve this, the rubber dam and adjacent parts need to be removed. Removal of the rubber dam allows for the introduction of foreign material, for instance bacteria, to enter the patient's tooth, potentially causing leakage and contamination of the field. In addition, it is quite difficult to fit the entire sensor holder on the underside of the rubber dam.

The biteplate portion of a typical sensor holder compounds the difficulties of properly placing the holder in the correct orientation and location because the clamp as well as the files rest in the occlusal field, also referred to as the biting surface of the tooth, which prevents the patient from biting down. Furthermore, the biteplate itself is a hindrance to acquiring useful radiographs because it prevents the patient from pushing the sensor into the vestibule to obtain a deep root image. Once the holder is finally placed under the dam, the alignment ring portion still needs to be slid into place for use by the x-ray cone. This has the adverse effect of agitating patients with the number and size of items in their mouth. Subjects commonly gag, have tongue thrusts, and misalign the imaging system, or compromise the operating field.

To prevent the issues discussed above, there is a need in the art for a sensor holding apparatus that can operate without a biteplate and which allows for compact, convenient sensor placement in the oral cavity with a variety of sensor shapes and dimensions so as to mitigate the problems associated with taking radiographs during dental surgeries. It is to these ends that the present invention has been developed.

SUMMARY OF THE INVENTION

To minimize the limitations in the prior art, and to minimize other limitations that will be apparent upon reading and understanding the present specification, the present disclosure describes an apparatus for holding a sensor, which may be placed inside a patient's oral cavity for use in dental imaging.

A sensor holding apparatus for facilitating dental imaging, in accordance with an exemplary embodiment of the present invention, comprises a handle an elongated shaft, longitudinally coupled to a distal end of the handle; and a sensor holder comprising a coupling component configured to removably attach to a portal end of the elongated shaft.

A sensor holder for dental imaging, in accordance with an exemplary embodiment of the present invention, comprises: a substantially flat body adapted to receive a sensor for capturing dental images; and a coupling component for removably attaching the sensor holder to a shaft or to an adapter configured to receive the sensor holder.

A sensor holding apparatus for facilitating dental imaging, in accordance with another exemplary embodiment of the present invention, comprises: a handle; an elongated shaft, longitudinally coupled to a distal end of the handle; and a sensor holder comprising a coupling component configured to removably attach to a portal end of the elongated shaft; wherein: the shaft comprises a cross-section adapted to receive a user's bite, the cross-section having a substantially polygonal perimeter; the sensor holder further comprises a substantially flat body having a substantially flat surface adapted for removably attaching a sensor to the sensor holder; and the coupling component is situated at a distal end of the substantially flat body of the sensor holder.

Furthermore, the substantially flat surface of the body of the sensor holder may comprise one or more connectors for removably attaching the sensor to the sensor holder, or the sensor holder may be configured to receive an adhesive for removably attaching the sensor to the sensor holder.

Additionally, the apparatus may further comprise an adapter for coupling the sensor holder to the elongated shaft in a manner so that the sensor holder may be positioned in a substantially periapical placement or in a substantially bitewing placement.

It is an objective of the present invention to facilitate taking dental images, for example, digital dental radiographs.

It is another objective of the present invention to eliminate the need for a patient to have to bite down on a biteplate to take accurate dental images.

It is yet another objective of the present invention to be able to orient a sensor and sensor holder in a plurality of ways so as to facilitate accurate imaging for all dental image types, for instance periapical and bitewing images.

It is yet another objective of the present invention to provide a less invasive and disruptive means to take digital dental radiographs during dental surgeries, such as root canals.

It is yet another objective of the present invention to utilize a handle with a specialized shaft to eliminate the use of common biteplates, thereby increasing the working space available to the dental practitioner performing a procedure in the oral cavity.

These and other advantages and features of the present invention are described herein with specificity so as to make the present invention understandable to one of ordinary skill in the art.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the sensor holding apparatus. Furthermore, elements that are known to be common and well understood to those in the industry are not depicted in order to provide a clear view of the various embodiments of the present invention.

FIG. 1(*a*) is a close-up view of a patient's mouth fitted with a rubber dam, in preparation for a root canal procedure. The rubber dam partially covers the patient's mouth, exposing only the tooth or teeth on which, in the illustrated case, endodontic work will be performed.

FIG. 1(*b*) is a close-up view of the root canal procedure of FIG. 1(*a*) as would be seen by a dental professional performing the procedure, wherein a sensor and sensor holding device in accordance with the present invention may be utilized to facilitate the procedure.

FIG. 3(*a*) depicts a sensor holding apparatus, in accordance with another exemplary embodiment of the present invention, wherein the sensor holder is shown coupled to a handle portion of the apparatus, via a shaft that comprises a coupling member.

FIG. 3(*b*) shows the sensor holding apparatus of FIG. 3(*a*), which has been retrofitted with an adapter for coupling a sensor holder at an alternative angle.

FIG. 3(*c*) is a close-up view of the adapter shown in FIG. 3(*b*).

FIG. 3(*d*) depicts various alternative cross-sections of a shaft, in accordance with different embodiments of the present invention.

FIG. 4(*b*) depicts a sensor holding apparatus, in accordance with another exemplary embodiment of the present invention, wherein the sensor holder is shown de-coupled from the apparatus for, for example, disposing of a used sensor holder.

FIG. 4(*c*) depicts a sensor holder and sensor holder receiving member, in accordance with an exemplary embodiment of the present invention, wherein the sensor holder comprises a coupling member for coupling with the sensor receiving member of the shaft shown in FIG. 4(*b*).

DETAILED DESCRIPTION OF THE INVENTION

Figure 2:
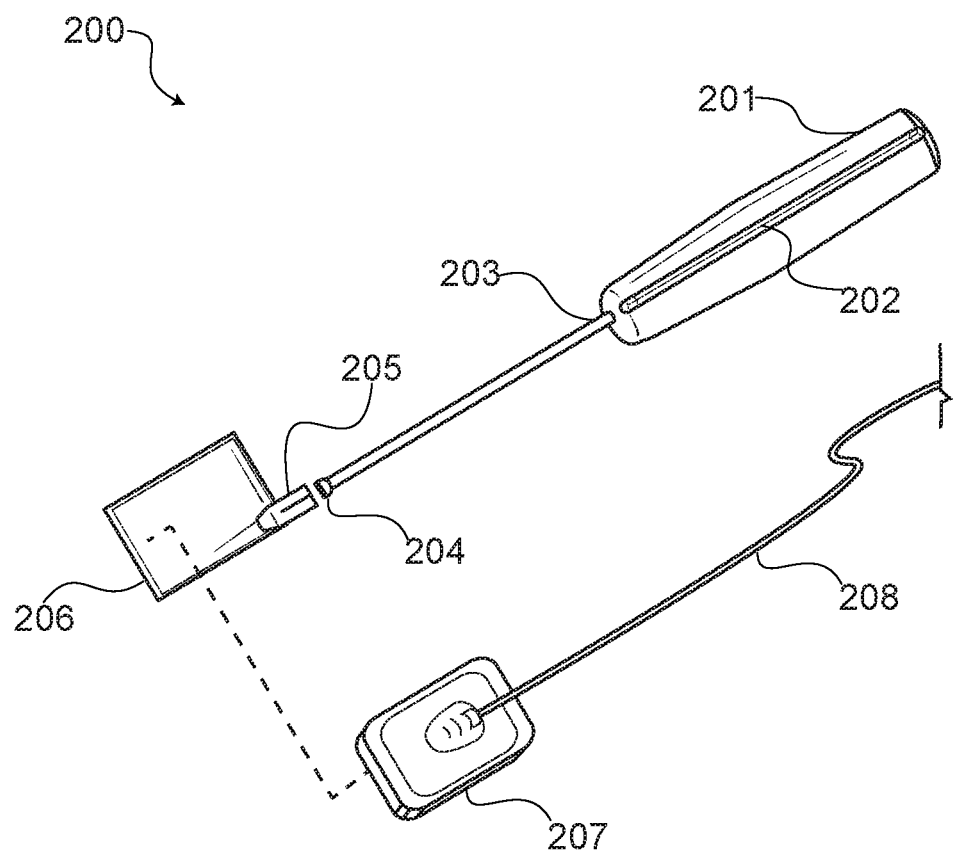
FIG. 2 depicts a sensor holding apparatus, in accordance with an exemplary embodiment of the present invention, comprising a sensor holder for attaching a radiograph sensor.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

An apparatus in accordance with the present invention comprises a removable sensor holder, which implements a specialized shaft to circumvent the need for commonly used biteplates, thereby increasing the working space available to the dental practitioner performing a procedure in the oral cavity. Such apparatus, and other embodiments of the present invention, are described and discussed in turn.

Primarily, FIGS. 1(a) and 1(b) show the environment in which a dentist, specialist, endodontist, or more generally a practitioner, will be performing their work. Hence, the environment in which use of the present invention is practiced is described first. FIG. 1(a) is a close-up view of a patient's mouth fitted with a rubber dam, in preparation for a root canal procedure. The rubber dam partially covers the patient's mouth, preferably exposing only a tooth or teeth within the oral cavity on which endodontic work will be performed. The figure specifically depicts dam 104, which has been placed to cover a patient's mouth, dam frame 105, which holds dam 104 in place, clamp 103 for holding the opening that exposes a patient's tooth or teeth, and exposed tooth 101, on which the specialist will be performing the procedure. Similarly, FIG. 1(b) is a close-up view of the root canal procedure depicted in FIG. 1(a) as would be seen by a dental professional performing the procedure, wherein a sensor and sensor holding device in accordance with the present invention may be utilized to facilitate the procedure.

As may be noted by both figures, there is not much room for a practitioner to work on tooth 101; since repeated radiographs are required during the procedure, a compact sensor holder in accordance with the present invention allows the practitioner to properly perform the procedure with greater ease than with the typically bulky sensor holding devices found in the prior art.

To create context for disclosing the present invention, a typical procedure such as a root canal is explained: Tooth 101 is typically a tooth that has likely become infected, especially in the nerve well below the tooth. At the top of tooth 101 is the enamel, with the crown residing just below the enamel. In treating tooth 101, it is typical to use one or more devices, such as a file, to perform the necessary procedure or treatment. Hence, tooth 101 has file 102 projecting downward through the center of the tooth, first through the enamel, then through the crown, dentin, and pulp, in that order. File 102 is a very thin tool with a shaft much like a needle, which is drilled through the layers of the tooth until reaching the nerve. However, file 102 or any other file provides little to no visible feedback as to the depth the dental professional has drilled. Thus, dental images, for example radiographs, are required throughout the filing process to determine how far the practitioner has drilled, and subsequently how much farther he or she needs to drill to reach the nerve.

Tooth 101 and file 102 take up some room in and around the oral cavity. Additionally, clamp 103, rubber dam 104, and rubber dam frame 105 add to the already cramp space. Thus, taking a dental image, for example a digital dental x-ray, which requires the use of a sensor that is also placed inside the patient's mouth, becomes an unnecessarily cumbersome process for various reasons.

For example, fitting additional tools or components such as film or sensors inside the oral cavity cause discomfort and pain to the patient. Furthermore, time is spent removing and reapplying rubber dam 104, and crowding in the oral cavity with dental tools and equipment, which makes it more difficult for the practitioner to perform their work, and may causes contamination of the operating field (such as tooth 111).

With regards to inefficiencies in the process of removing and reapplying rubber dam 104 when taking progressive radiographs, the following process for application of rubber dam 104 is presented as evidence. To place rubber dam 104, clamp 103 is first placed on tooth 101 undergoing treatment or on the tooth behind it using forceps. Clamp 103 has a pair of jaws which are laterally opposed and are connected by a bridge. The jaws grip the tooth on the buccal (cheek) and the lingual (tongue) side of the tooth right above the gum line. A small hole is punched into rubber dam 104, typically approximately two millimeters by two millimeters, although the hole can vary in size depending on the surgeon's preference. Rubber dam 104 is then secured in a proper position around the tooth by placing it over clamp 103 and around tooth 101 or the adjacent tooth. The hole of rubber dam 104 shrinks snugly around tooth 101 and the crown stands out from the hole in rubber dam 104. Then, rubber dam frame 105 is placed at the outer periphery of rubber dam 104 and outside the patient's mouth, in order to keep rubber dam 104 firmly in place.

Rubber dam 104 is kept in place by an integrally incorporated rubber dam frame 105, both of which are necessarily removed when using a sensor holding apparatus in the prior art. Hence, many of the steps of this process need to be repeated a plurality of times in a single root canal procedure if a sensor holding apparatus present in the prior art is utilized. By contrast, a more compact sensor holding apparatus, in accordance with the present invention does not require removal of rubber dam 104; this is accomplished primarily by eliminating the need of a traditional bitewing, and incorporating a special shaft or handle, which serves the same purpose as a biteplate, but without the need for the additional component typical of the prior art.

Biteplates are present on most holders for digital dental radiographs, including both periapicals and bitewings. These biteplates, in addition to the tendency to induce gagging, are also difficult to adjust once set in place. Doing so requires either the patient or technician to reach into the oral cavity of the patient and readjust the biteplate, frequently prompting supplementary gagging. Additionally, a biteplate has a static relationship with the sensor holder it is attached to. As such, it becomes problematic to take some dental images where the shape, size, or alignment of the jaw or teeth is abnormal or simply different than the biteplate is equipped to handle. The present invention eliminates a biteplate, instead including a handle with a specialized shaft, whereby the patient or technician need only move the handle to customize each image to the oral cavity of the patient. Furthermore, the specialized shaft circumvents the need for the commonly used biteplates, thereby increasing the working space available to the dental practitioner performing the procedure in the oral cavity.

It is important to note that the advantages and applications of the proposed invention are not limited to root canal procedures, or more generally, endodontic treatments, but are in fact preferential for general dental imaging such as radiographs or x-rays. This means that the present invention may be implemented in a variety of procedures outside of surgeries, for instance at dental checkups, as well.

Turning now to the remaining figures, FIG. 2 depicts a sensor holding apparatus, in accordance with an exemplary embodiment of the present invention, comprising a sensor holder for attaching a sensor such as a radiograph sensor. Sensor holding apparatus 200 comprises: handle 201, which includes cable groove 202; shaft 203, which further comprises a sensor holder receiving member (or first coupling component 204); and sensor holder 205, which further comprises a sensor holder coupling member (or second coupling component 206) for coupling with shaft 203.

Handle 201 is typically roughly cylindrical in shape with cable groove 202 disrupting the cylindrical shape and forming a cavity along its length in a region roughly equivalent to the dimensions of a traditional cable line, such as one that may be found on a typical radiograph sensor. Cable groove 202 allows sensor cable 208 of sensor 207 to be held securely in place. This feature simply keeps the wire or cable that extends from such sensors, from getting in the way of a practitioner during a procedure. In one embodiment, handle 201 does not include cable groove 202, however, cable groove 202 may be desirable as a means to keep sensor cable 208 out of a practitioner's way. In embodiments wherein cable groove 202 is a feature of handle 201, cable groove 202 may secure a sensor cable in a number of ways. For example, and without limiting the scope of the present invention, one cable groove 202 secures sensor cable 208 through physical pressure. Alternatively, sensor cable 208 may be held in place within cable groove 202 using any other known means such as a locking mechanism.

Handle 201 may be constructed of a number of materials without limiting or deviating from the scope of the present invention. For example, handle 201 may be constructed of plastic, nylon, metal, wood, or any other material that may be formed or may is moldable into a shape that is easy to hold. Typically, a synthetic thermoplastic polymer can be used to form an adequate shape, however any other material may be utilized without departing from the scope of the present invention. Additionally, handle 201 may differ from the approximate cylindrical shape of the embodiment shown in FIG. 2, and may have any other shape that is suitable for placing a hand over handle 201 and manipulating apparatus 200. In alternative embodiments, handle 201 may be of similar thickness and material to shaft 203, however, in an exemplary embodiment, handle 201 comprises a plastic material ergonomically shaped to allow for easy and comfortable manipulation of apparatus 200. Handle 201 may be used with any dental imaging, though it is particularly useful for obtaining images such as those which are defined by a periapical view of the oral cavity because of its parallel orientation to sensor holder 206.

Shaft 203 is connected to handle 201 and typically extends in a straight, forward direction out of handle 201, though other embodiments exist. For example, and without limiting or deviating from the scope of the present invention, shaft 203 may be S-shaped, L-shaped, or angled. In an exemplary embodiment however, shaft 203 is straight and extends away from one end of handle 201 in linear form so as to form a predominantly straight line—this way, less space is taken by apparatus 200, when inserted inside a patent's mouth or oral cavity during a procedure, making it easier on the patient, and facilitating a more efficient procedure for the practitioner.

Shaft 203 may be constructed of the same material, or a different material as handle 201. Hence, shaft 203 may be constructed of metal, plastic, or any other material that offers durability and stability for holding a sensor. Furthermore, shaft 203 may comprise a cross-sectional shape that is configured to allow a patient to easily bite down on shaft 203 so as to stabilize apparatus 200 during the taking of a radiograph or x-ray. The shape of such a cross-section or surface area of shaft 203 may comprise a variety of forms without deviating from the scope of the present invention, but several forms or shapes are discussed in more detail below, with reference to FIG. 3(*d*); for example, in an exemplary embodiment, shaft 203 has a substantially hexagonal cross-section for allowing a patient to easily bite down on apparatus 200.

Shaft 203 comprises first coupling component 204, which may be separate or integral with shaft 203. First coupling component 204 is adapted to connect sensor holder 205 to handle 201 so that a practitioner may manipulate sensor 207 (once attached to sensor holder 205) during a procedure that requires radiographs or x-rays. In the pictured embodiment, first coupling component 204 is integral with shaft 203 and is located on the distal end of shaft 203. First coupling component may be constructed of a different material or the same material as shaft 203. As stated above, first coupling component 204 may be a separate part from shaft 203, or may be a feature that forms an integral part of shaft 203. For example, and without limiting the scope of the present invention, first coupling component may be a socket (see FIG. 4(*c*)) or a protrusion (see FIG. 4(*e*)) that extends and forms an integral part of shaft 203.

Sensor holder 205 is shaped in a manner so as to accommodate a typical radiograph sensor used in taking x-rays from a patient. For example, and without limiting the scope of the present invention, sensor holder 205 has a substantially rectangular shape that is long enough and wide enough to receive the flat end of sensor 207. However, sensor holder 205 may comprise of any shape without deviating from the scope of the present invention, so long as it has a surface area adequate enough to receive and be coupled to a typical sensor, such as sensor 207. As with the other components of apparatus 200, sensor holder 205 may be constructed of a variety of materials so long as sensor holder 205 is durable and strong enough to sustain the weight of sensor 207. In an exemplary embodiment, sensor holder 205 is constructed from a material such as a plastic so that it is inexpensive, yet durable, and may be designed for disposable use. In another embodiment, sensor holder 205 is constructed so that it is resistant to sterilizing equipment, and hence sensor holder 205 may be easily sterilized in a practitioner's office or clinic.

Sensor holder 205 further comprise second coupling component 206, which is configured to connect or couple with first component 204. Second component 206 and first component 204 connect sensor holder 205 and shaft 203 in a manner so that apparatus 200 is stable and sturdy enough for a practitioner to manipulate sensor 207 into and out of a patient's oral cavity. Like first component 204, second component 206 may comprise a separate part from sensor holder 205 or may form an integral part with sensor holder 205. For example, and without limiting the scope of the present invention, second component 206 may comprise a substantially flat protrusion extending from a predominantly rectangular body, for example, see FIG. 4(*b*). Alternatively, second coupling component 206 may comprise a shape that forms a socket affixed to sensor holder 205 in a manner so that it is adapted to receive a complimentary coupling component, for example, see FIG. 4(*d*) and FIG. 4(*e*).

When sensor holding apparatus 200 is fully assembled, first coupling component 204 is coupled to second coupling component 206 so that apparatus 200 is sturdy. This may be accomplished with several known methods without deviating from the scope of the present invention. For example, first coupling component 204 and second coupling component 206 may couple by way of friction and pressure created among the two components when coupled together. Alternatively, first coupling component 204 and second coupling component 206 may be coupled together with magnets, adhesives, interlocking mechanisms, or any other method so long as a sturdy, reliable coupling is established.

Sensor holder 205 may be either disposable or sterilizable and may be removably or permanently affixed to sensor 207. In embodiments which employ a disposable sensor holder 205, a closed contamination sleeve may be employed then removed along with sensor holder 205 from shaft 203 and handle 201 after usage. In alternative embodiment, a protective sheath may be placed around disposable sensor holder 205 and sensor 207. Preferably, sensor holder 205 is disposable and will comprise relatively weak materials, such as but not limited to plastic or nylon, which may be manufactured with more cost efficient means than stronger, longer lasting materials meant for repeated use and recurring sterilizations. Alternatively, as stated above, a protective sheath such as those well known in the art may be utilized when reusable materials will be implemented to construct sensor holder 205.

Affixation of sensor 207 to sensor holder 205 may occur in a plurality of ways—for example, sensor holder 205 may comprise one or more adhesive materials, which affixes sensor 207 to sensor holder 205 when pressed together with sufficient force. Alternatively, sensor 207 may comprise one or more adhesive materials, which may affix sensor 207 to sensor holder 205 when pressed together with sufficient force. These and other methods for affixing, coupling or attaching a sensor to a sensor holder in accordance with the present invention, are disclosed in more detail below, particularly with reference to FIG. 4(*k*) and FIG. 4(*l*). In an exemplary embodiment, sensor holder 205 is disposable and comprises an adhesive material used to affix sensor 207 to sensor holder 205. Possible compositions of the adhesive material include, but are not limited to, epoxy, acrylics, cyanoacrylates, silicones, hot melt, tape, polyurethanes, pressure-sensitive adhesives, contact adhesives, or any other type of known adhesive suitable to hold a sensor securely in place, and allow for the removal of the sensor after use.

Turning to the next figure, FIG. 3(*a*) is a sensor holding apparatus, in accordance with another exemplary embodiment of the present invention, wherein the sensor holder is shown coupled to a handle portion of the apparatus, via a shaft that comprises a coupling member. Sensor holding apparatus 300 is similar in functionality to sensor holding apparatus 200, with a few notable differences henceforth elaborated upon.

Sensor holding apparatus 300 comprises similar components as apparatus 200, including a handle, shaft, sensor holder, and coupling components that allow the sensor holder and shaft to be coupled and de-coupled for cleaning or to replace the sensor holder. Of course, an apparatus for holding a sensor in accordance with the present invention could be constructed as a single unit, eliminating any removable part or components, without deviating from the scope of the present invention. While such embodiment could be a useful disposable embodiment, current prices and manufacturing costs of producing such disposable devices, it may be more desirable for apparatus 300 to comprise several components so that only a smaller component, for example holder 304, is disposable and hence the remaining components reusable.

Apparatus 300 may also comprise of removably coupled parts or components so that apparatus 300 is adaptable to a variety of sensor holder types. For example, it may be desirable to allow for retrofitting apparatus 300 with interchangeable sensor holders configured for different angled or positioned radiographs. This interchangeable feature may be accomplished in any number of ways without limiting or deviating from the scope of the present invention. For example, shaft 303 may be configured so that it can be inserted into a portion of sensor holder 304 in a manner similar to those disclosed in reference to FIG. 2.

In one embodiment, shaft 303 comprises an end portion that is angled at 90 degrees. Alternatively, angled second or first coupling members may be implemented either to the sensor holder or the shaft, respectively.

In an exemplary embodiment, as shown, in FIG. 3(b) apparatus 300 is coupled to sensor holder 304, via adapter 302, which is configured to couple to both shaft 303 and sensor holder 304 by receiving both coupling components of the shaft and the sensor holder. Adapter 302 is angled at 90 degrees and comprises ends for receiving a first and a second coupling component, such as first coupling component 204 and second coupling component 205. It should be noted that adapter 302 is just one embodiment of the present invention, and that in other embodiments, shaft 303 may be integral with or form the 90 degree angled adapter so that shaft 303 can be coupled with sensor holder 304 at the desired angle (for example, see FIG. 6(a)).

FIG. 3(c) is a close-up view of adapter 302 and depicts its elements. Adapter 302 is a component of a sensor holding apparatus in accordance with the present invention, which may be utilized with apparatus 300. Adapter 302 comprises two ends that are adapted for coupling with shaft 303 and sensor holder 304. As depicted, adapter 302 comprises a sensor holder receiving end (or end 310) for coupling with sensor holder 304, and a shaft receiving end (or end 311) for receiving shaft 303. Adapter 302 typically has a curved or hooked configuration that substantially forms a 90-degree angle, which as stated above, makes it useful for making bitewing-oriented digital dental radiographs. This facilitates for example, obtaining images of the lower half of the maxillary teeth and upper half of the mandibular teeth, including the crowns of those teeth.

As stated above, adapter 302 is a separate piece from shaft 303 and sensor holder 304, and may be removably affixed to shaft 303 and sensor holder 304. Nevertheless, it is to be understood that other means of achieving the same result may be implemented without deviating from the scope of the present invention. For example, in an alternative embodiment, sensor holder 304 may have a second coupling end that substantially forms a 90-degree angle. In yet another embodiment, shaft 303 has a curved first coupling member that substantially forms a 90-degree angle. Either way of providing a different angled position for accommodating different types of desired images of a patient may be implemented without limiting or deviating from the scope of the present invention.

Adapter 302 does not limit which digital dental radiographs may be taken if it is included as a component of the present invention. In an exemplary embodiment, adapter 302 is L-shaped, though the orientation or exact dimensionality of the L-shape is not to be limited. Adapter 302 may be of either identical or different material or dimensionality than shaft 303 and any of its components.

Turning to the next figure, FIG. 3(d) depicts various alternative cross-sections of a shaft, in accordance with different embodiments of the present invention. As mentioned above, a shaft in accordance with the present invention may be cylindrical or comprise of any other shape adapted for allowing a patient to bite down on apparatus 300 in order to help the practitioner hold the sensor still and achieving proper angulations of the sensor inside the patient's mouth.

In an exemplary embodiment, shaft 303 includes shaft cross section 305, which is shaped in a hexagonal shape so as to provide a substantially cylindrical circumference that includes various flat planes that aid a patient's bite to securely hold the shaft still. This configuration may be desirable because having no flat planes or surfaces may cause shaft 303 to swivel from side to side during the taking of the dental image, hence having to require the practitioner to take and retake the desired image. Additionally, this polygonal shaped perimeter of the shaft facilitates proper angulations of the sensor. Other cross-sectional shapes may be implemented without limiting or deviating from the scope of the present invention, and a few possible configurations are shown as examples in FIG. 3(d) next to cross-section 305. For example, and without limiting the scope of the present invention, shaft 303 may comprise of a cross-section adapted to receive a user's bite, wherein the cross-section forms a substantially polygonal perimeter, such as a hexagonal shape, a square shape, an octagonal shape, or any other shape that may be easily held by a patient's bite and or facilitate proper angulations of the sensor.

Turning now to FIGS. 4(a)-4(l), other embodiments of a sensor holding apparatus are discussed, with particular focus on various possible embodiments for a sensor holder in accordance with the present invention.

Figure 4A:
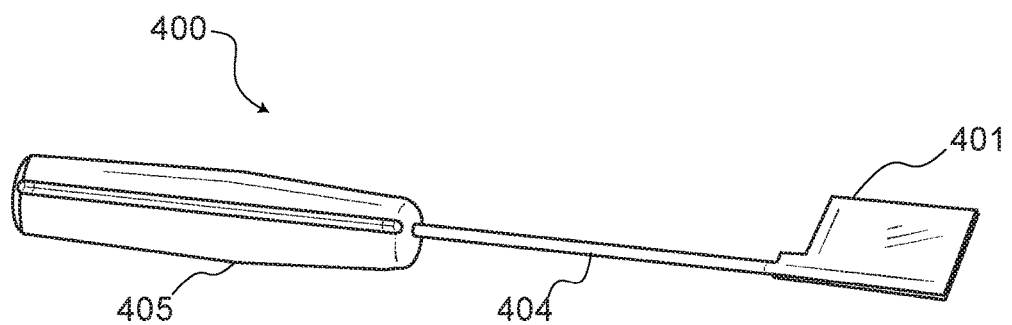
FIG. 4(*a*) depicts a sensor holding apparatus, in accordance with one embodiment of the present invention, wherein the sensor holder forms an integral part of the apparatus, and more specifically, wherein the sensor holder is permanently attached to the shaft.
FIG. 4(d) depicts a side view of the sensor holder and sensor holder receiving member shown in FIG. 4(c).
FIG. 4(e) depicts a sensor holder and sensor holder receiving member, in accordance with an exemplary embodiment of the present invention, wherein the sensor holder comprises a substantially flat coupling member for coupling with the sensor receiving member of the shaft shown in FIG. 4(b), except the flat coupling member is positioned so that it is perpendicular to the longer side of the sensor holder.
FIG. 4(f) depicts a side view of the sensor holder and sensor holder receiving member shown in FIG. 4(e).
FIG. 4(g) depicts a sensor holder and sensor holder receiving member, in accordance with another exemplary embodiment of the present invention, wherein the sensor holder receiving member comprises a substantially flat protrusion extending from the shaft.
FIG. 4(h) depicts a side view of the sensor holder and sensor holder receiving member shown in FIG. 4(g).
FIG. 4(i) depicts a sensor holder and sensor holder receiving member, in accordance with yet another exemplary embodiment of the present invention.
FIG. 4(j) depicts a side view of the sensor holder and sensor holder receiving member shown in FIG. 4(i).
FIG. 4(k) depicts yet another embodiment of a sensor holder in accordance with the present invention, wherein the sensor holder comprises at least one connector for holding a sensor in place.
FIG. 4(l) is a side-view of the sensor holder shown in FIG. 4(k), wherein the sensor holder comprises at least one retention member, or connector, for holding a sensor in place.

FIG. 4(a) depicts a sensor holding apparatus, in accordance with one embodiment of the present invention, wherein the sensor holder forms an integral part of the apparatus, and more specifically, wherein the sensor holder is permanently attached to the shaft. As shown in FIG. 4(a), sensor holding apparatus 400 comprises handle 405, which includes shaft 404. Integral with shaft 404, is sensor holder 401, which includes a flat surface for receiving a digital radiograph sensor.

As mentioned above, a sensor holding apparatus in accordance with the present invention may comprise a single unit and need not include detachable components such as a removably coupled sensor holder. However, it is typically desirable to provide removable components, including a removable sensor holder, so that these various removable components can be constructed in a less expensive manufacturing process, including for the purposes of making said components disposable.

Figure 4B:
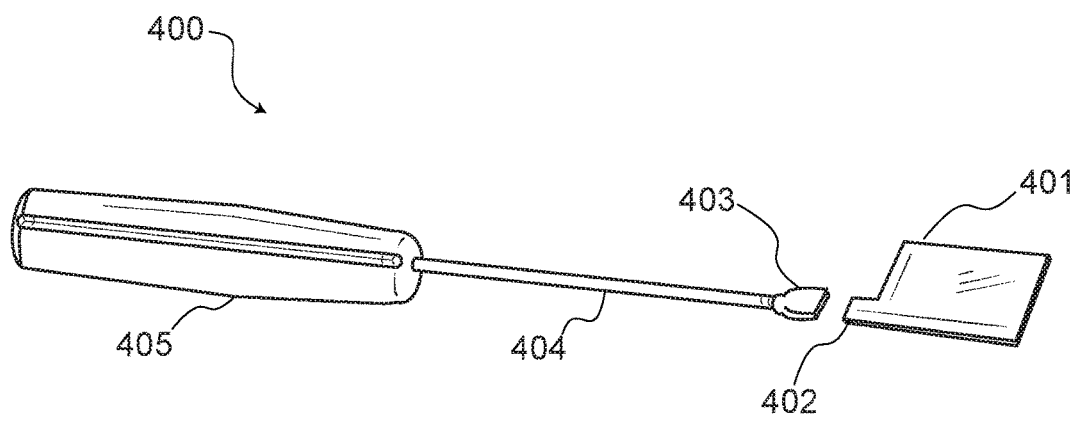

FIG. 4(b) depicts a sensor holding apparatus, in accordance with one exemplary embodiment of the present invention, wherein the sensor holder is shown de-coupled from the apparatus for disposing of a used sensor holder.

Sensor holding apparatus 400 comprises similar components as those of the embodiments mentioned above, including a handle, a shaft, a coupling component for coupling a sensor holder, and a sensor holder configured to be coupled to a handle that includes a shaft. Specifically, apparatus 400 comprises sensor holder 401, which further comprises a sensor holder coupling member 402 for coupling with shaft 404. As other embodiments, apparatus 400 includes handle 405, which includes shaft 404, and coupling component 403 for coupling with sensor holder 401.

Focusing now on sensor holder 401, sensor holder 401 includes a flat surface for attaching or affixing a digital sensor. As mentioned above sensor holder 401 may be either disposable or sterilizable. In embodiments which employ a disposable sensor holder 401, a closed contamination sleeve may be employed then removed along with sensor holder 401 from shaft 403 and handle 405 after usage. In another embodiment, a protective sheath may be placed around disposable sensor holder 401 and the sensor affixed to sensor holder 401. In an exemplary embodiment, a disposable sensor holder 401 will comprise relatively weak materials, such as but not limited to plastic or nylon. If utilized along with a protective sheath, the material of the protective sheath would be known by a person of ordinary skill in the art. In an exemplary embodiment, sensor holder 401 is disposable and comprises an adhesive material used to affix a sensor to sensor holder 401. Possible compositions of the adhesive material include, but are not limited to, epoxy, acrylics, cyanoacrylates, silicones, hot melt, tape, polyurethanes, pressure-sensitive adhesives, contact adhesives, or any other type of known adhesive suitable to hold a sensor securely in place, and allow for the removal of the sensor after use.

Furthermore, sensor holder 401 is typically removably coupled to shaft 404 by any number of coupling components, such as coupling components 402 and 403. Typically, coupling component 402 may have a shape resembling an inverse or complementary shape as that of coupling component 403. For example, and without limiting or deviating from the scope of the present invention, coupling component 402 could comprise the shape of a circle, triangle, parallelogram, pentagon, hexagon, or any other shape so long as it is complementary in shape to coupling component 403—in order for the two parts to fit together securely. In the exemplary embodiment exemplified in FIG. 4(b), coupling component 402 has a flat rectangular shape, and coupling component 403 has a complementary flat rectangular shape adapted to receive coupling component 402.

It is understood that the configuration of the coupling components that bring together sensor holder 401 and shaft 404 are not limited to those described herein, and any other configuration possible would not deviate from the scope of the present invention. For example, as shown in FIG. 4(b) coupling component 402 may be inserted into coupling component 403. Alternatively, as shown in the various examples that follow, coupling component 402 could be configured to receive coupling component 403.

Figure 4C:
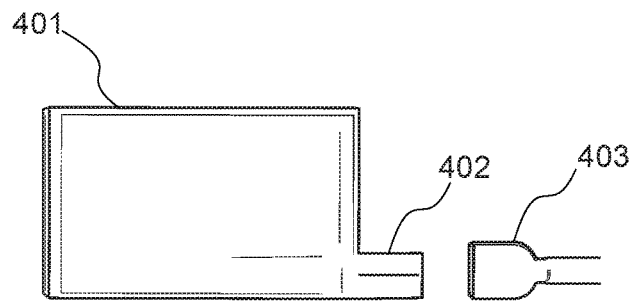

FIG. 4(c) depicts a sensor holder with a coupling component 402, and sensor holder receiving member or coupling component 403, in accordance with an exemplary embodiment of the present invention. In this exemplary embodiment, the sensor holder comprises a substantially flat surface, and a substantially flat protrusion that extends outwardly from its surface to form coupling member 402 for coupling with the sensor receiving member (coupling member 403) of shaft 404 as shown in FIG. 4(b).

Figure 4D:
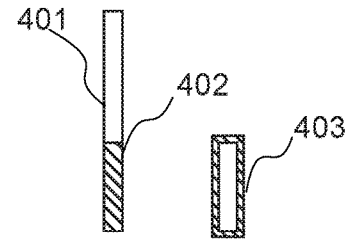

FIG. 4(d) depicts a side view of the sensor holder and sensor holder receiving member shown in FIG. 4(c), depicting how sensor holder 401 and the sensor receiving member of shaft 404 (coupling component 403) may be coupled together, in accordance with another embodiment of the present invention. In this exemplary embodiment, coupling component 402 and coupling component 403 are positioned along a longitudinal axis of the sensor holder, wherein the coupling members each comprise a substantially flat protrusion. This vertical orientation allows for an efficient use of space, as a horizontal orientation (i.e. a latitudinal configuration) may add more bulk to apparatus 400. On the other hand, a latitudinal configuration may be desirable if, for example, a sturdier construction of sensor holder 401 may be achieved when implementing a latitudinal configuration. Such latitudinal configurations are described below as alternative embodiments of the present invention.

Figure 4E:
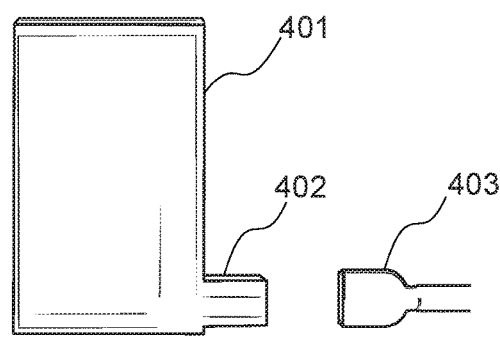

Turning first to the following figure however, FIG. 4(e) depicts a sensor holder and sensor holder receiving member, in accordance with an exemplary embodiment of the present invention. In the exemplary embodiment shown, sensor holder 401 comprises a substantially flat coupling member—coupling member 402, for coupling with sensor receiving member (coupling member 403) of the shaft. In this embodiment, the flat coupling member is positioned so that it is perpendicular to the longer side of sensor holder 401; this configuration allows for taking dental radiographs at a different angle or position.

Figure 4F:
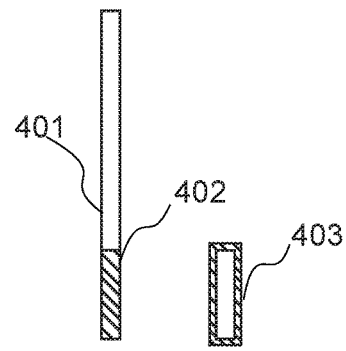

Similarly, FIG. 4(f) depicts a side view of the sensor holder and sensor holder receiving member shown in FIG. 4(e), depicting how the sensor holder and sensor receiving member may be coupled together, in accordance with one embodiment of the present invention, wherein the coupling member and receiving member are positioned along a longitudinal axis of the sensor holder.

Figure 4G:
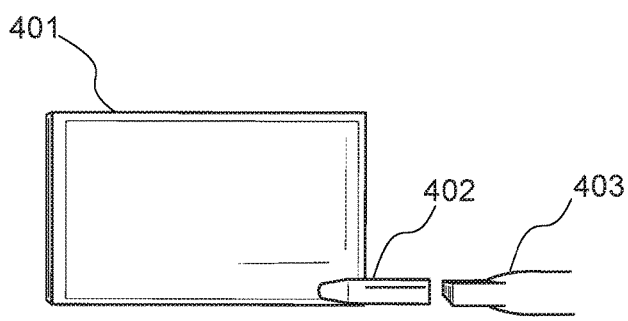
Figure 4H:
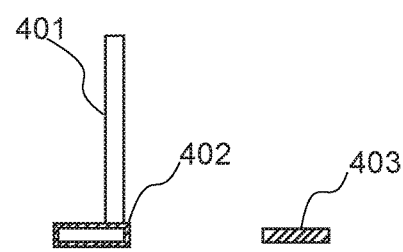

FIG. 4(g) depicts a sensor holder and sensor holder receiving member, in accordance with another exemplary embodiment of the present invention, wherein the sensor holder receiving member comprises a substantially flat receiving member for coupling with the sensor holder coupling member. Similarly, FIG. 4(h) depicts a side view of the sensor holder and sensor holder receiving member shown in FIG. 4(g), wherein the coupling member and receiving member are positioned along a latitudinal axis of the sensor holder, and wherein the receiving member comprises a substantially flat protrusion.

Figure 4I:
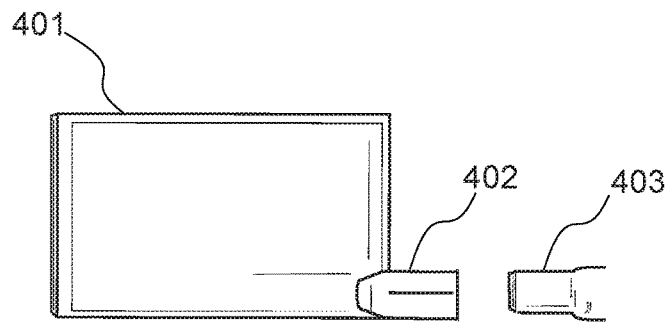

To expand on the various embodiments that may be implemented in accordance with the present invention, FIG. 4(i) depicts a sensor holder and sensor holder receiving member, in accordance with another exemplary embodiment of the present invention, wherein the sensor holder coupling member (coupling component 402) and sensor holder receiving member (coupling component 403), are positioned along a longitudinal axis of the sensor holder as in FIG. 4(d) and FIG. 4(f), but wherein the coupling component 403 comprises a substantially flat protrusion, and coupling component 402 is adapted to receive said protrusion.

Figure 4J:
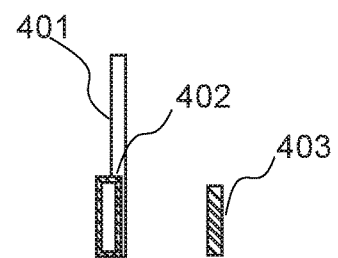

Similarly, FIG. 4(j) depicts a side view of the sensor holder and sensor holder receiving member shown in FIG. 4(i). In this exemplary embodiment, coupling components 402 and 403, once coupled, remain coupled through friction. In such an embodiment, coupling component 403 may be minutely smaller in dimension than coupling component 402 so that each component is forced through friction and pressure to remain coupled until sufficient deliberate force is applied to decouple the components. In an alternative embodiment, friction is not the primary factor keeping components 402 and 403 coupled, but instead a locking mechanism may be implemented. For example, and without limiting or deviating from the scope of the present invention, other locking mechanisms may be snapped, clicked, slid, or otherwise locked into place. Whatever mechanism is implemented, typically, reversal of the step performed to couple coupling component 402 and coupling component 403 decouples the two components, and a new usable sensor holder 401 may be coupled to shaft 404.

Figure 4K:
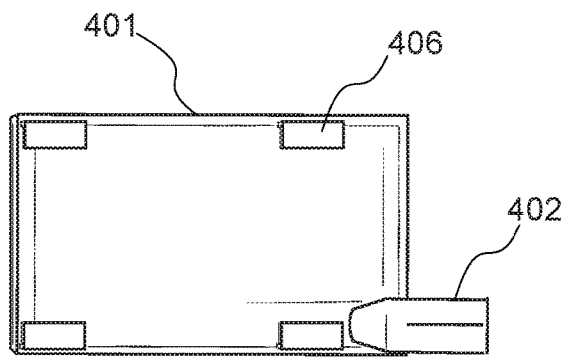
Figure 4L:
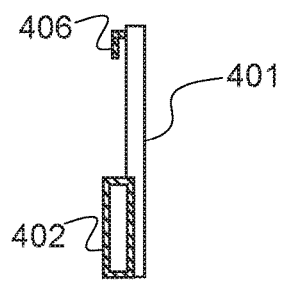
Figure 5A:
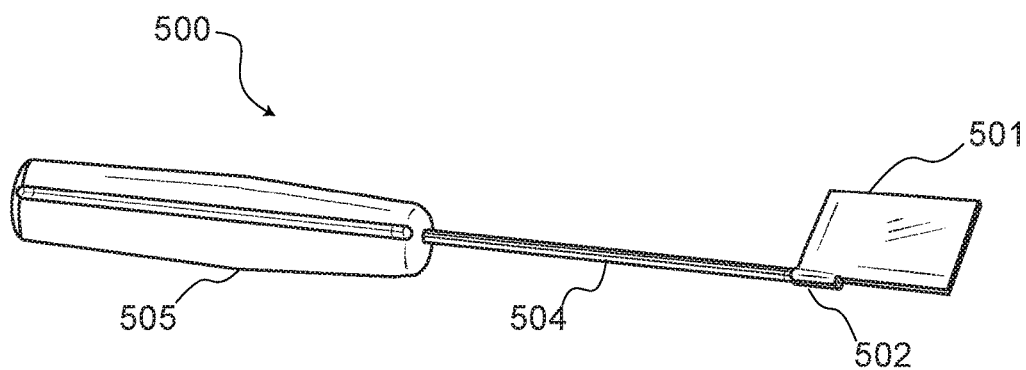
FIG. 5(a) depicts a sensor holding apparatus, in accordance with another exemplary embodiment of the present invention. In this embodiment, the sensor holder allows for quick and easy use of different orientations, and is shown in a horizontal periapical configuration.
Figure 5B:
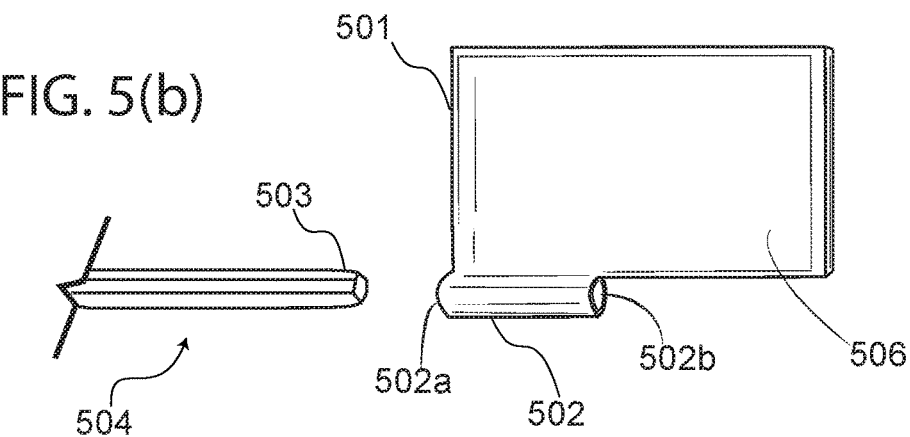
FIG. 5(b) depicts the sensor holder receiving end of a shaft, and the sensor holder shown in FIG. 5(a), wherein the sensor holder comprises a coupling member for coupling with the sensor receiving end of the shaft. In this embodiment, the sensor's coupling member is adapted to couple with the sensor receiving in multiple ways.
Figure 5C:
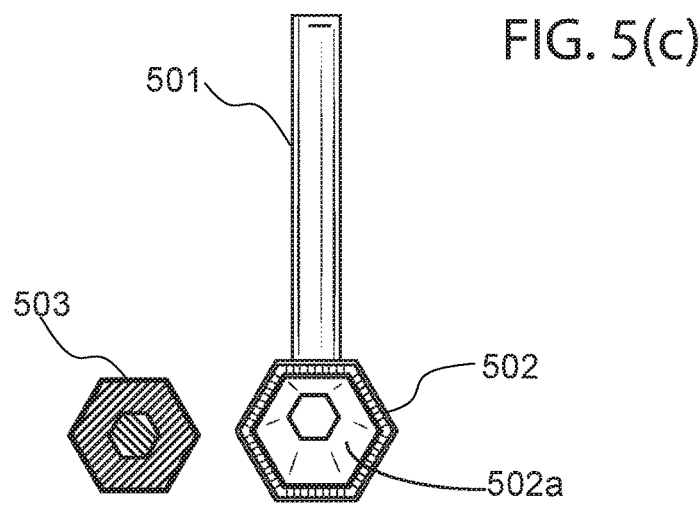
FIG. 5(c) depicts a side view of the sensor holder and sensor holder receiving end shown in FIG. 5(b).
Figure 5D:
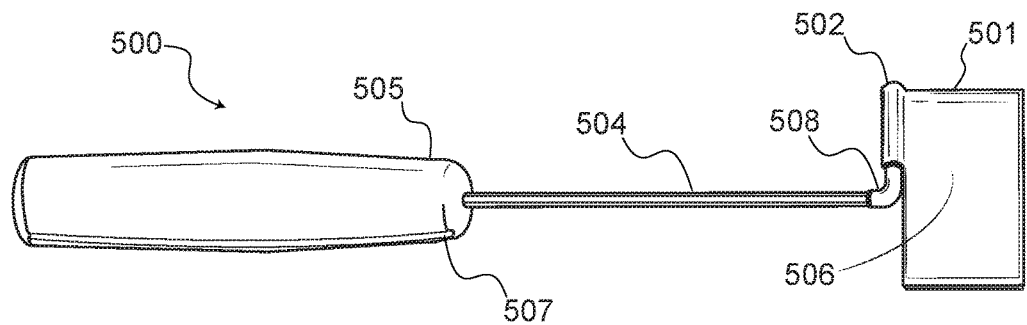
FIG. 5(d) depicts the sensor holder apparatus shown in FIG. 5(a), wherein the sensor holder is coupled in a manner so that it is positioned in a bitewing vertical configuration, with the aid of an adapter.
Figure 5E:
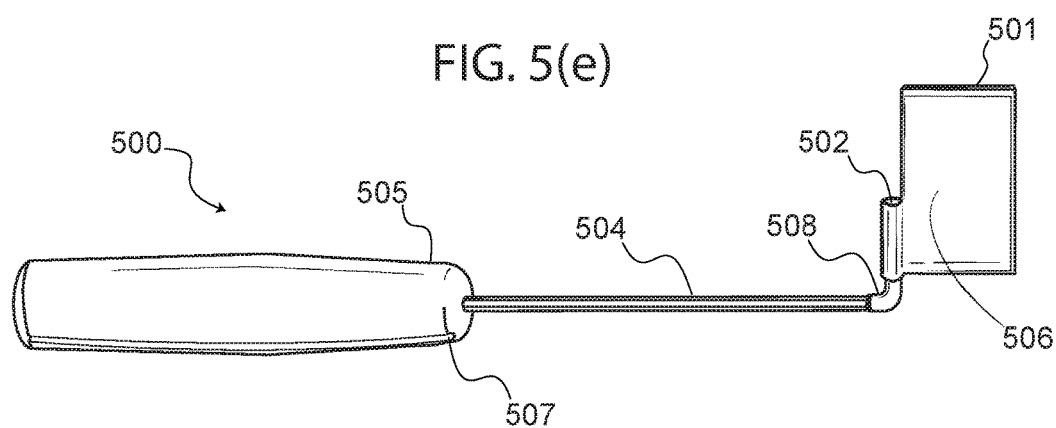
FIG. 5(e) depicts the sensor holder apparatus shown in FIG. 5(a), wherein the sensor holder is coupled in a manner so that it is positioned in a periapical vertical configuration, with the aid of an adapter.
Figure 5F:
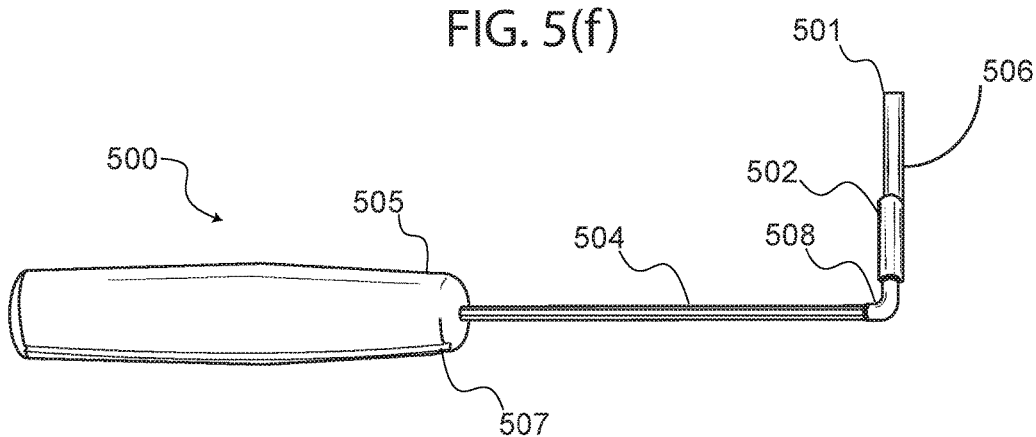
FIG. 5(f) depicts the sensor holder apparatus shown in FIG. 5(a), wherein the sensor holder is coupled in a manner so that it is positioned in an anterior periapical configuration, with the aid of an adapter.

FIG. 4(k) depicts yet another embodiment of the sensor holding apparatus shown in FIG. 4(b), wherein sensor holder 401 comprises at least one retention member, or connector, for holding a sensor in place. Sensor holder 401, with reference to FIG. 4(*k*), comprises coupling component 402 and at least one of connectors 406. Connectors 406 may be desirable for securing a sensor such as sensor 207 to sensor holder 401. In the pictured embodiment, there are four retention members or connectors 406, with one connector roughly in each corner of sensor holder 401. However, any number of connectors or retention members may be implemented without limiting or deviating from the scope of the present invention. For example, a retention member may comprise of multiple connectors along the edges of a surface of the sensor holder. Alternatively, a retention member may be a grooved edge at the perimeter of the surface of the sensor holder. This edge, or retention member, may be configured to receive the sensor and hold the sensor securely against the flat surface by creating a pressure. In the shown embodiment, the retention member comprises of connectors 406.

Connectors 406 may be designed to hold sensors with deference to the various shapes and sizes of x-ray sensors on the market. In an exemplary embodiment, connectors 406 may be curved or angled substantially parallel to the flat surface on sensor holder 401 on which a sensor may be affixed. As shown in FIG. 4(*l*) one of connectors 406 has been positioned to allow for a sensor to be held in place by pressure exerted between the connector and the sensor. In the embodiment shown, a sensor may be slid into place parallel to the orientation of sensor holder 401 then secured by the pressure asserted by each of the connectors 406. Furthermore, connectors may be located in any location on sensor holder 401 and many shapes or configurations may be implemented without limiting or deviating from the scope of the present invention. For example, connectors 406 may comprise additional devices to hold a sensor in place in addition to or the alternative to utilizing pressure; they may implement locking mechanisms, magnetic mechanisms, or any other type of device that may be configured for removably attaching a sensor to sensor holding apparatus 400. As such, connectors 406 as depicted in FIG. 4(*k*) and FIG. 4(*l*) are merely illustrative and not exhaustive or required by sensor holding apparatus 400.

In other embodiments, a sensor may be coupled to sensor holder 401 by utilizing edge pressure achieved by a grooved molding that is integral with the body of sensor holder 401. In such embodiment, a retention member may comprise, not connectors, but a molding that may be shaped so as to receive a sensor and hold it against the surface of sensor holder 401 by pressure. Such moldings are well known and may be easily implemented with sensor holder 401 by one skilled in the art.

Turning next to FIGS. 5(*a*) through 5(*f*), another exemplary embodiment of a sensor holder apparatus is described. In this embodiment, the sensor holder may be adapted in a variety of configurations so that a practitioner may utilize a single type of sensor holder for different types of dental images. FIG. 5(*a*) depicts a sensor holding apparatus, in accordance with another exemplary embodiment of the present invention. In this embodiment, the sensor holder allows for quick and easy use of different orientations, and is shown in a horizontal periapical configuration.

Sensor holder apparatus 500 comprises sensor holder 501, which is removably coupled to shaft 504 of handle 505. Shaft 504 comprises a sensor holder receiving end, or coupling member 503. Similar to the embodiments described above, shaft 504 has a cross section that comprises a hexagonal shape, which allows a patient to securely hold apparatus 500 in a desired position, by receiving the patient's teeth so that the shaft does not rotate but stays in a fixed position. Coupling member 503 is typically one end of shaft 504 that has been adapted to engage or mate with sensor holder 501.

Sensor holder 501 comprises a body that includes flat surface 506 for placing an adhesive in order to attach a sensor. Furthermore, sensor holder 501 further comprises coupling member 502, which in this embodiment is a protruding portion that forms an opening on two ends (502*a* and 502*b*) and is adapted to receive coupling member 503 from either end 502*a* or end 502*b*. This allows sensor holder 501 to be dynamic, in that a practitioner may utilize sensor holder 501 in several configurations. Additionally, in various embodiments, coupling member 503 may be mated with coupling member 502 in a manner so that coupling member 503 of shaft 504 extends about mid-length of sensor holder 501 by inserting coupling member 503 through both ends 502*a* and 502*b*. In this manner, the apparatus affords the practitioner greater flexibility when maneuvering the sensor inside the patient's mouth.

FIG. 5(*b*) depicts the sensor holder receiving end of shaft 504 (i.e. coupling member 503) and sensor holder 501, showing ends 502*a* and 502*b* of coupling member 502. In another view, FIG. 5(*c*) depicts the sensor holder and sensor holder receiving end shown in FIG. 5(*b*), illustrating how coupling member 503 may be inserted or mated with coupling member 502 by inserting it on end 502*a* of coupling member 502.

FIG. 5(*d*) depicts the sensor holder apparatus shown in FIG. 5(*a*), wherein the sensor holder is coupled in a manner so that it is positioned in a bitewing vertical configuration, with the aid of adapter 508. Similar to adapter 302, adapter 508 is configured so that a 90-degree angle may be formed. This allows for a variety of configurations that are desirable to a practitioner.

In FIG. 5(*d*), and the remaining figures, adapter 508 is shown as a male to female adapter. However, it should be noted that adapter 508 may be a male to male, a female to female, or any other type of adapter suitable for mating a shaft portion of the apparatus to the sensor holder itself. FIG. 5(*e*) depicts the sensor holder apparatus shown in FIG. 5(*a*), wherein the sensor holder is coupled in a manner so that it is positioned in a periapical vertical configuration, with the aid of adapter 508. FIG. 5(*f*) depicts the sensor holder apparatus shown in FIG. 5(*a*), wherein the sensor holder is coupled in a manner so that it is positioned in an anterior periapical configuration, with the aid of adapter 508. In each of the configurations, it should be noted that handle 505 of sensor holder apparatus 500, may be positioned so that cable groove 507 secures the cable of a sensor for attaching to the apparatus, in a manner so that it is out of the way.

Turning to the final set of figures, FIG. 6(*a*) depicts yet another sensor holding apparatus shown in a horizontal periapical configuration, wherein the sensor holder and shaft include alternative embodiments in accordance with the present invention. Sensor holding apparatus 600 comprises sensor holder 601, which is illustrated in an exploded view decoupled from shaft 604*a* of handle 605. As with other embodiments, handle 605 includes cable groove 607 positioned along a length of handle 605.

In this embodiment, sensor holder 601 includes a coupling component 602 that is positioned (similar to previously discussed embodiments) along a longitudinal edge or perimeter of sensor holder 601. As with previous embodiments of a sensor holder in accordance with the present invention, sensor holder 601 also includes a substantially flat planar body adapted to receive a sensor for capturing dental images, the planar body defined by a first flat surface and a second flat surface on opposite sides of a single plane (i.e. flat surface 606 is one of such surfaces adapted to receive a sensor such as a radiograph sensor).

Coupling component 602 facilitates removably attaching sensor holder 601 to shaft 604a, and may comprise a tubular member positioned along a longitudinal edge of the planar body of sensor holder 601, the tubular member including two openings configured to register with the cylindrical protrusion (603) of shaft 604a so that the handle, the shaft, and the longitudinal edge of sensor holder 601 lie in a straight line. In alternative embodiments, where an adapter is implemented or where the shaft is angled or curved (see FIGS. 5(d)-(f), and FIG. 6(c) respectively), the sensor holder maybe positioned in either a bitewing vertical configuration or a periapical vertical configuration.

As mentioned above, shaft 604a includes a substantially cylindrical protrusion 603, which may have a different circumference than the remaining length of shaft 604a. For example, and without limiting the scope of the present invention, shaft 604a may include an elongated body with a first portion having a first diameter and a first length that predominantly extends from handle 605, and a second portion having a second diameter and a second length that extends from a terminal end of shaft 604a that is opposite of handle 605 and that includes a substantially cylindrical protrusion configured to register with a coupling component of sensor holder 601. One benefit of this embodiment is that the different circumferences of the elongated body of shaft 604a, may prevent sensor holder 601 from undesirably sliding too much towards handle 605.

As mentioned above, sensor holder 601 is similar to other embodiments previously discussed, however sensor holder 601 includes an exemplary embodiment of a coupling member wherein a substantially tubular protrusion further includes an opening or longitudinal slit that allows improved flexibility for the component resulting in a tighter fit around the receiving portion of shaft 604a (or coupling component 603), and to facilitate removal. Spacing B on FIG. 6(a) illustrates this opening or slit, and is further described in turn with reference to FIG. 6(b).

Figure 6A:
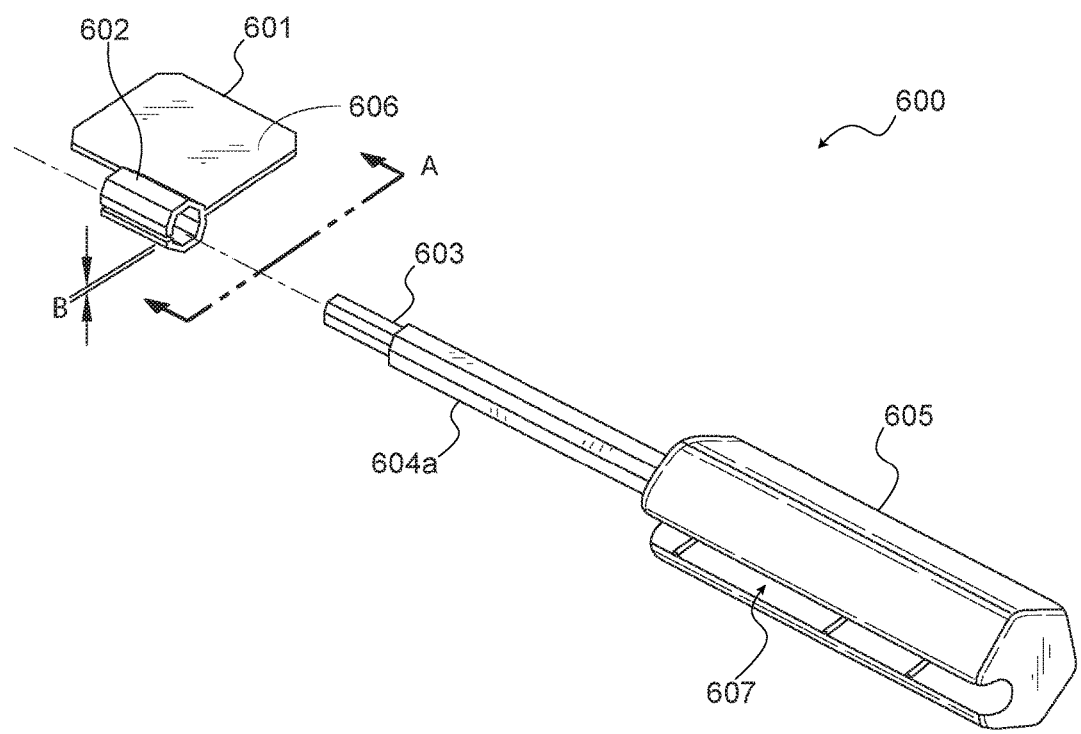
FIG. 6(a) depicts yet another sensor holding apparatus shown in a horizontal periapical configuration, wherein the sensor holder and shaft include alternative embodiments in accordance with the present invention.
Figure 6B:
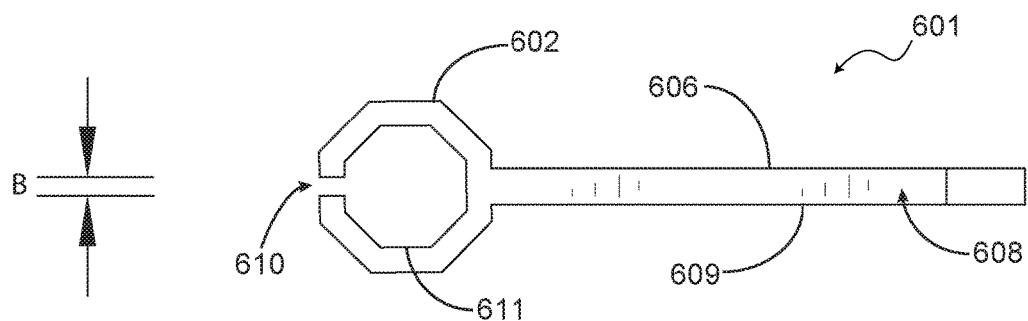
FIG. 6(b) depicts a side view of the sensor holder shown in FIG. 6(a).

FIG. 6(b) depicts a side view of the sensor holder shown in FIG. 6(a), illustrating a view taken along line A. From this view, it can be appreciated that (as in previously discussed embodiments) sensor holder 601 includes an uninterrupted and continuous planar body 608, having a first flat surface (e.g. 606) and a second flat surface (e.g. 609) on opposite sides of a single plane. From a terminal end, and along a longitudinal edge of the planar body 608, coupling component 602 is formed as an elongated tubular protrusion, which extends from an edge of the planar body 608 of sensor holder 601. In this exemplary embodiment, coupling component 602 includes an opening or slit 610 that comprises a spacing B, which disrupts an otherwise complete circumference formed by the hollow tubular protrusion that forms coupling component 602. As mentioned above, slit 610 may facilitate removal of sensor holder 601 from protrusion 603, and in some embodiments, the circumference of coupling component 602 is such that sensor holder 601 may fit tightly and securely around protrusion 603.

Although various embodiments may include different shapes and sizes, in an exemplary embodiment, an inner surface 611 of coupling component 602 may be shaped so as to register with cylindrical protrusion 603 of shaft 604a. As such, in exemplary embodiments, inner surface 611 may form a substantially polygonal cross-section or perimeter inside coupling component 602 that matches a polygonal cross-section of a coupling component of the shaft. As mentioned above, such polygonal cross-section may comprise a hexagonal cross-section so as to prevent the sensor holder from sliding or slipping, and to allow a patient to easily bite down on a portion of the shaft of the device.

Figure 6C:
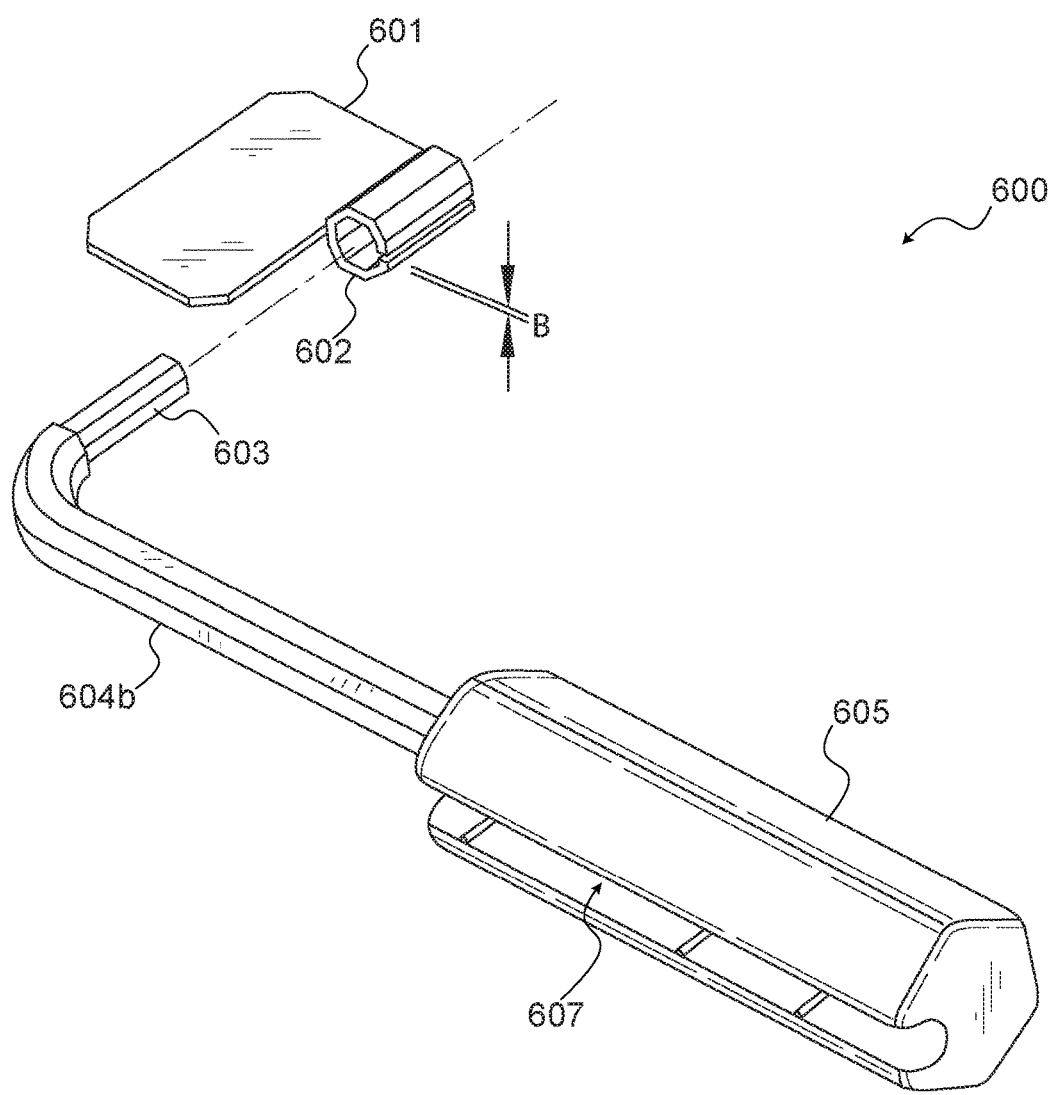
FIG. 6(c) depicts yet another sensor holding apparatus including a shaft configured to position the sensor holder in either a bitewing vertical configuration or a periapical vertical configuration.

FIG. 6(c) depicts yet another sensor holding apparatus including a shaft configured to position the sensor holder in either a bitewing vertical configuration or a periapical vertical configuration. In this embodiment, rather than requiring an adapter, as disclosed above, shaft 604b may be implemented with apparatus 600 to include an elongated body that form a substantially 90-degree curve. Moreover, because sensor 601 may include two openings on either terminal end of coupling component 602, the sensor may be positioned in a bitewing vertical configuration (as shown) or in a periapical vertical configuration (i.e. by flipping the sensor in the opposite direction).

Finally, shaft 604b may be constructed of the same material, or a different material as handle 605. Hence, shaft 604b may be constructed of metal, plastic, or any other material that offers durability and stability for holding a sensor. Furthermore, in exemplary embodiments, shaft 604b may be constructed of a material that allows shaft 604b to be bendable or flexible so that at least a portion of shaft 604b; specifically, in exemplary embodiments, the terminal end including cylindrical protrusion 603 may be bendable between and outside of a 180-degree and 90-degree positions so that protrusion 603 may be positioned at a 90-degree angle, straight, or any other angled configuration with respect to handle 605.

Finally, a sensor holder apparatus in accordance with the present invention may implement additional features that are commonly known in the art for purposes of compatibility with other existing components. For example, and without deviating from the scope of the invention, add-on components such as a cone alignment may be implemented, in order to configure the sensor holding apparatus for alignment with imaging apparatus.

A sensor holding apparatus has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

DESCRIPTION OF THE REFERENCE SYMBOLS

101: Tooth
102: File
103: Clamp
104: Rubber dam
105: Rubber dam frame
200: Sensor holding apparatus
201: Handle
202: Cable groove
203: Shaft
204: First coupling component
205: Sensor holder
206: Second coupling component
207: Sensor
208: Sensor cable
300: Sensor holding apparatus
301: Handle
302: Adapter 303: Shaft
304: Sensor Holder
305: Shaft cross-section
310: End
311: End
400: Sensor holding apparatus
401: Sensor Holder
402: Coupling component
403: Coupling component
404: Shaft
405: Handle
406: Connectors
500: Sensor holding apparatus
501: Sensor Holder
502: Coupling component
503: Coupling component
504: Shaft
505: Handle
506: Flat surface
507: Cable groove
508: Adapter
600: Sensor holding apparatus
601: Sensor holder
602: Coupling component
603: Coupling component
604a: Shaft
604b: Shaft
605: Handle
606: Flat surface
607: Cable groove
608: Planar body
609: Flat surface
610: Slit
611: Inner surface

What is claimed is:

1. A sensor holder for facilitating dental imaging, comprising:
a planar body configured to receive a sensor for capturing dental images, the planar body defined by a first flat surface and a second flat surface on opposite sides of a single plane; and
an elongated tubular protrusion for removably attaching the sensor holder to a shaft configured to receive the sensor holder, the elongated tubular protrusion situated along a longitudinal edge of the planar body, wherein the sensor holder excludes any ancillary structures other than the planar body and the elongated tubular protrusion.

2. The sensor holder of claim 1, wherein the elongated tubular protrusion includes a longitudinal slit that disrupts a circumference formed by the elongated tubular protrusion.

3. The sensor holder of claim 1, wherein the elongated tubular protrusion includes openings situated at two terminal ends, the openings configured to receive a portion of the shaft.

4. The sensor holder of claim 1, wherein the elongated tubular protrusion includes an inner surface having a polygonal cross-section.

5. The sensor holder of claim 4, wherein the polygonal cross-section comprises a hexagonal shape.

6. The sensor holder of claim 1, wherein the planar body of the sensor holder includes an adhesive on the first flat surface for attaching the sensor to the sensor holder.

7. The sensor holder of claim 1, wherein the planar body of the sensor holder comprises at least one edge configured to receive the sensor and hold the sensor securely against the first flat surface by creating a pressure.

8. The apparatus of claim 1, wherein the tubular elongated protrusion of the sensor holder extends up to mid-length along the longitudinal edge of the planar body of the sensor holder.

9. A sensor holding apparatus for dental imaging, comprising:
a handle;
a shaft comprising a first end and a second end, wherein the first end is longitudinally coupled to the handle; and
a sensor holder, comprising:
a planar body configured to receive a sensor for capturing dental images, the planar body defined by a first flat surface and a second flat surface on opposite sides of a single plane; and
an elongated tubular protrusion for removably attaching the sensor holder to the second end of the shaft, the elongated tubular protrusion situated along a longitudinal edge of the planar body, wherein the sensor holder excludes any ancillary structures other than the planar body and the coupling component.

10. The apparatus of claim 9, wherein the shaft comprises an elongated body that is straight.

11. The apparatus of claim 9, wherein the shaft comprises an elongated body that forms a 90-degree angle and is configured to couple with the sensor holder in a manner so that the sensor holder is positioned in a periapical placement or in a bitewing placement in both horizontal or vertical orientations.

12. The apparatus of claim 9, wherein the shaft comprises an elongated body with a first portion having a first diameter and a first length that predominantly extends from the handle, and a second portion having a second diameter and a second length that extends from the terminal end of the shaft that is opposite of the handle.

13. The apparatus of claim 9, wherein the shaft comprises a portion that includes a cross-section configured to receive a user's bite.

14. The apparatus of claim 13, wherein the cross-section configured to receive the user's bite comprises a polygonal perimeter.

15. The apparatus of claim 14, wherein the polygonal cross-section comprises a hexagonal shape.

16. The apparatus of claim 9, wherein the elongated tubular protrusion includes a slit that disrupts an otherwise complete circumference formed by the tubular protrusion.

17. The apparatus of claim 9, wherein the elongated tubular protrusion includes openings situated at two terminal ends, the openings configured to receive a portion of the shaft.

18. The apparatus of claim 9, wherein the elongated tubular protrusion includes an inner surface having a polygonal cross-section configured to register with a portion of the shaft.

19. The apparatus of claim 9, wherein the planar body of the sensor holder includes an adhesive on the first flat surface for attaching the sensor to the sensor holder.

20. The apparatus of claim 9, wherein at least a portion of the shaft is bendable so that the shaft is configured to bend and be positioned at a 90-degree angle, straight, or any other angle with respect to the handle.

* * * * *